(12) United States Patent
Wariar et al.

(10) Patent No.: US 7,002,670 B2
(45) Date of Patent: Feb. 21, 2006

(54) OPTICAL SENSOR AND METHOD FOR MEASURING CONCENTRATION OF A CHEMICAL CONSTITUENT USING ITS INTRINSIC OPTICAL ABSORBANCE

(75) Inventors: Ramesh Wariar, Tampa, FL (US); Li Pan, Tampa, FL (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 231 days.

(21) Appl. No.: 10/167,796

(22) Filed: Jun. 12, 2002

(65) Prior Publication Data

US 2003/0231294 A1    Dec. 18, 2003

(51) Int. Cl.
*G01N 33/48* (2006.01)

(52) U.S. Cl. .................... 356/39; 356/432; 356/436

(58) Field of Classification Search ............ 356/39–41, 356/432, 433, 435, 436, 440, 441, 442; 250/573, 250/574; 435/4, 5, 7, 26, 808
See application file for complete search history.

(56) References Cited

U.S. PATENT DOCUMENTS

| | | | | |
|---|---|---|---|---|
| 3,881,992 A | * | 5/1975 | Ralston ........................ 435/3 |
| 4,816,393 A | | 3/1989 | Siedel et al. .................. 435/18 |
| 4,954,435 A | * | 9/1990 | Krauth ...................... 435/7.93 |
| 5,252,488 A | * | 10/1993 | Purdie ......................... 436/71 |
| 5,331,958 A | * | 7/1994 | Oppenheimer .............. 600/322 |
| 5,348,003 A | | 9/1994 | Caro .......................... 600/310 |
| 5,527,708 A | | 6/1996 | Blass .......................... 436/98 |
| 5,602,038 A | | 2/1997 | Kell ........................... 436/98 |
| 5,602,647 A | * | 2/1997 | Xu et al. ..................... 356/435 |
| 5,733,787 A | | 3/1998 | Messenger et al. ........... 436/98 |
| 5,772,606 A | | 6/1998 | Ashibe et al. ............... 600/573 |
| 5,815,260 A | | 9/1998 | Dou et al. ................... 356/301 |
| 5,822,071 A | | 10/1998 | Dosmann et al. ........... 356/435 |
| 5,858,644 A | * | 1/1999 | Chen ............................. 435/4 |
| 5,958,786 A | | 9/1999 | Munkholm .................. 436/98 |
| 6,028,311 A | | 2/2000 | Sodickson et al. .......... 250/343 |
| 6,044,285 A | | 3/2000 | Chaiken et al. ............. 600/316 |
| 6,087,182 A | | 7/2000 | Jeng et al. ..................... 436/66 |

(Continued)

FOREIGN PATENT DOCUMENTS

WO    WO 96/18096    6/1996

(Continued)

OTHER PUBLICATIONS

Patent Abstracts of Japan Publication No. 62228145 dated Jul. 10, 1987 entitled "Ultraviolet Type Organic Substance Measuring Apparatus".

(Continued)

*Primary Examiner*—Layla G. Lauchman
(74) *Attorney, Agent, or Firm*—Joseph P. Reagen; Bell, Boyd & Lloyd LLC

(57) ABSTRACT

An improved optical sensor and method for measuring concentration of a chemical constituent where measurement interference from other chemical compounds is present in the solution is provided. More specifically, the invention relates to a system for measuring the amount of creatinine in effluent dialysate during, before, or following a kidney dialysis procedure and a method for using the same. Alternatively, the method may be used with blood and other body fluids or solutions that contact the patient. The system may use an enzyme or other chemical process to specifically remove or convert an analyte with an intrinsic optical absorbance. By measuring the absorbance before and after the chemical process the analyte can be measured with high accuracy and specificity. The method may be extended to multiple analyte measurements using cascaded chemical processes.

21 Claims, 10 Drawing Sheets

U.S. PATENT DOCUMENTS

| | | | | |
|---|---|---|---|---|
| 6,107,083 | A | 8/2000 | Collins et al. | 435/288.7 |
| 6,151,522 | A | 11/2000 | Alfano et al. | 600/473 |
| 6,241,863 | B1 | 6/2001 | Monbouquette | 205/777.588 |
| 6,262,798 | B1 * | 7/2001 | Shepherd et al. | 356/39 |
| 6,268,910 | B1 * | 7/2001 | Samsoondar et al. | 356/39 |
| 6,306,660 | B1 | 10/2001 | Messenger et al. | 436/88 |
| 6,788,414 | B1 * | 9/2004 | Yeung et al. | 356/436 |

FOREIGN PATENT DOCUMENTS

| | | | |
|---|---|---|---|
| WO | WO 01/53806 | A1 * | 7/2001 |
| WO | WO 02/01195 | A1 * | 1/2002 |

OTHER PUBLICATIONS

Li et al. article entitled "Sol-gel encapsulation of lactate dehydrogenase for optical sensing of L-lactate" *Biosensors & Bioelectronics* 17 (2002) pp. 323-330.

Rosa et al. article entitled "Optical biosensor based on nitrite reductase immobilized in controlled pore glass" *Biosensors & Bioelectronics* 17 (2002) pp. 45-52.

* cited by examiner

OPTICAL SENSOR AND METHOD FOR MEASURING CONCENTRATION OF A CHEMICAL CONSTITUENT USING ITS INTRINSIC OPTICAL ABSORBANCE

BACKGROUND OF THE INVENTION

The present invention generally relates to an improved optical sensor and method for measuring the concentration of a chemical constituent in a biological fluid where measurement interference from other chemical constituents is present. More specifically, the invention relates to a system for measuring online a concentration of one or more analytes, such as creatinine and urea, in biological fluids, such as blood, body secretions, or fluids from clinical therapies, such as dialysis solution, (i.e. dialysate) and a method for using the same. The sensor measures optical absorbance of a fluid sample to determine a concentration of an analyte. Optical absorbance measurements may then be compared to optical absorbance measurements taken after a process that specifically targets and removes the analyte. Because the process removes the intrinsic absorbance of the analyte, a resulting change in optical absorbance may be used to measure the analyte concentration.

Creatinine is produced in muscle as a metabolic waste product and is present in serum, and other body fluids. Because serum creatinine concentration is inversely correlated to kidney function, creatinine measurement in serum and urine is one of the most common clinical tests ordered. Also, creatinine kinetics measured during renal therapies can be used to estimate solute removal efficiency and to estimate patient lean body mass—an index of patient malnutrition (Forbes G, and Bruining G J, Urinary creatinine excretion and lean body mass. Am J Clin Nutr 29: 1359, 1976; Keshaviah P R et al. Lean body mass estimation from creatinine kinetics, Journal of the American Society of Nephrology, 4, 7, 1994, pg. 1475–85).

Creatinine biosensors reported in the prior-art generally consist of two components: a chemical recognition component that targets only creatinine (with high specificity) and converts it into a measurable product, and a transducer component that detects and measures the product. The chemical recognition component may be, for example, biocatalytic (i.e. an enzyme), and the transducer may be, for example, electrochemical (e.g. amperometric, voltametric), or optical (absorbance, or fluorescence measurement) Examples of biosensors constructed using these technologies are available in literature (Killard A J, Smyth M R. Trends in biotechnology, 18(10), 2000, pg. 433–37).

The most common creatinine sensors are biocatalytic and based on measuring the products formed from one or more enzymatic reactions. Multi-enzyme biosensors (Tombach B. et al. Clinica Chimica Acta. 312(1–2):129–34, 2001; Rui C-S et al. Analytical biochemistry, 210 163–171, 1993) are more complex than single-enzyme biosensors because of their requirement of coupled reactions with enzymes and substrates. Prior-art single-enzyme catalysed reactions are based on the measurement of $NH_3$ or $NH_4^+$ which is accomplished using either optical transduction (H. Li et al. Biosensors & Bioelectron. 7, 725–732, 1992) or electrochemical transduction (JP57074097 Measurement of creatinine and device therefore, 1982). However, these traditional single-enzyme biosensors are also disadvantageous because: 1) in addition to an enzyme, the optical measurement requires a separate (i.e. extrinsic) chemical indicator (calorimetric, fluorometric) for $NH_3$ measurement that must be stable and accurate for the measurement duration (3 to 4 hours during dialysis); and 2) electrochemical transduction is invasive, prone to drift, and requires repeated sensor calibration.

A need, therefore, exists for a creatinine sensor that is less complex than the prior art and can be used for stable online measurements of creatinine in applications such as dialysis. Although the instrinsic ultraviolet (UV) absorbance of creatinine is well known (Adams W S et al. Analytical Chemistry, vol. 34, No. 7, 1962) a suitable biosensor that utilizes this intrinsic absorbance to measure creatinine in biological fluids has not been feasible because of the broad and overlapping absorbance spectra of many co-existing solutes. The applicants have found that a simple and accurate creatinine sensor can be constructed if absorbance measurements are combined with a process that specifically targets and removes creatinine.

SUMMARY OF THE INVENTION

The present invention generally relates to an improved optical sensor and method for measuring a concentration of a chemical constituent where measurement interference from other chemical constituents is present in the solution. More specifically, the invention relates to a system for measuring online the concentrations of analytes such as creatinine and urea in fluids such as blood, body secretions, or from clinical therapies e.g. dialysis solution (i.e. dialysate) and a method for using the same. The system and the method measures creatinine from the disappearance of its intrinsic optical absorbance as a result of enzymatic hydrolysis. The sensor and the method, although illustrated for creatinine, may be extended to other solutes like urea (which has an optical absorbance in the infrared spectrum), and in fluids other than dialysate. Further, instead of biocatalytic conversion, selective chemical binding with affinity membranes or molecular imprinted polymers (T Panasyuk-Delaney et al. Proc. $1^{st}$ International Workshop on Molecular Imprinting, UK 2000 pg. 45; Subrahmanyam S et al. Biosensors & Bioelectronics 16 (2001) 631–7) may also be used as the chemical recognition component.

To this end, in an embodiment of the present invention, a system for measuring an analyte in a biological fluid using its intrinsic optical absorbance is provided. The system has a light source forming an optical beam that is directed on the fluid sample. The system further has a process that selectively removes the intrinsic absorbance of the analyte in the fluid sample wherein the fluid sample has a first optical absorbance before the process and further having a second optical absorbance after the process. Finally, the system has a light detector receiving the optical beam directed through the fluid sample to produce a first signal indicative of the first optical absorbance and receiving the optical beam directed through the fluid sample after the process to produce a second signal indicative of the second optical absorbance.

In an embodiment, a computer or microprocessor compares the first optical absorbance to the second optical absorbance.

In an embodiment, a first cuvette is provided through which the fluid sample is directed.

In an embodiment, a second cuvette is provided through which the fluid sample is directed after exposing the sample to the enzyme.

In an embodiment, the enzyme is creatinine deiminase.

In an embodiment an enzyme other than creatinine deiminase may be used.

In an embodiment, creatinine deiminase is immobilised on a substrate.

In an embodiment, a beamsplitter is provided in the route of the optical beam.

In an embodiment, a mirror is provided in the route of the optical beam reflecting the optical beam to the light detector.

In an embodiment, a pump is provided combining the fluid sample with the enzyme.

In an embodiment, one or more valves may be used to successively bring the sample before and after enzymatic conversion in to a single cuvette across which optical measurements are made.

In an embodiment, the change in absorbance may be measured in a cuvette dynamically during the chemical process, for example, when the sample is in contact with the enzyme.

In another embodiment of the present invention, a method for measuring creatinine is provided. The method has the steps of: pumping the fluid containing the analyte through an optical beam; detecting a first optical absorbance of the fluid; bringing the fluid in contact with an enzyme; detecting a second optical absorbance of the fluid; and comparing the first optical absorbance to the second optical absorbance.

In an embodiment, the method provides the step of directing the optical beam with an optical waveguide.

In an embodiment, the method provides the step of directing the optical beam with a mirror.

In an embodiment, the method provides the step of directing the optical beam with a beam splitter.

In an embodiment, the method provides the step of obtaining the fluid sample from a hemodialyzer.

In an embodiment, the method provides the step of obtaining the fluid sample from a patient.

In an embodiment, the method provides the step of intermittently measuring the first optical absorbance and the second optical absorbance.

In an embodiment, the method provides the step of continuously measuring the first optical absorbance and the second optical absorbance.

In an embodiment, the measurement is made at one or more wavelengths.

In an embodiment, an optical spectrum is transformed using mathematical transforms.

In an embodiment, optical components may be molded from a single plastic component.

In an embodiment, the enzyme is creatinine deiminase.

In an embodiment, selective chemical binding process is used instead of the enzyme.

In an embodiment, the effluent dialysate sample contains several solutes with overlapping absorbance spectra that produce measurement interference.

It is, therefore, an advantage of the present invention to provide a system and a method which provides online measurements of creatinine in effluent dialysate.

Another advantage of the present invention is to provide a system for measuring creatinine in effluent dialysate and a method for measuring creatinine that uses an enzyme.

Yet another advantage of the present invention is to provide a system for measuring creatinine in effluent dialysate and method for measuring creatinine that uses optical absorbance for measurement.

Moreover, an advantage of the present invention is to provide a system for measuring creatinine in effluent dialysate and a method for measuring creatinine using continuous or intermittent measurements of the dialysate during dialysis.

A further advantage of the present invention is to provide a system for measuring creatinine in effluent dialysate and a method for measuring creatinine with less pH interference and measurement drift than conventional methods.

Another advantage of the present invention is to provide a system for measuring creatinine in effluent dialysate and a method for measuring creatinine which does not require fluorescent or calorimetric indicators for $NH_3$ measurement.

A still further advantage of the present invention is to provide a system for measuring creatinine in effluent dialysate and a method for measuring creatinine requiring one enzyme.

Yet another advantage of the present invention is to provide a system for measuring creatinine in effluent dialysate and a method for measuring creatinine which is cost-effective.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to an improved optical sensor and method for measuring the concentration of a chemical constituent using its intrinsic absorbance. More specifically, the invention relates to a system for measuring online the concentration of analytes such as creatinine and urea in fluids such as blood, body secretions, or from clinical therapies e.g. dialysis solution (i.e. dialysate) and a method for using the same. The system measures the creatinine concentration from the disappearance of its intrinsic optical absorbance as a result of enzymatic hydrolysis. Creatinine is present in effluent dialysate along with several uremic retention products, for example, uric acid, uracil, and hippuric acid (Vanholder R et al. The uraemic syndrome, Replacement of renal function by dialysis, Ed. Jacobs C, Kjellstrand C M, Koch K M, 4$^{th}$ Ed., Kluwer Acad. Pub. Pg. 12). The presence of these and other co-absorbing solutes make the optical absorbance measurement of creatinine typically difficult.

The present invention measures creatinine concentration using its intrinsic optical absorbance. The change in absorbance of effluent dialysate measured before and after creatinine hydrolysis using an enzyme such as creatinine deiminase may be used to measure creatinine. This is possible because creatinine has a relatively large intrinsic optical absorbance, and the end products of the creatinine deiminase reaction (i.e. N-methylhydantoin and $NH_3$) have different absorbance spectra compared to creatinine. Similarly, the system and the method herein described may be used to measure other analytes, such as, for example, urea, uracil and hippuric acid that have known intrinsic absorbance.

Figure 1:
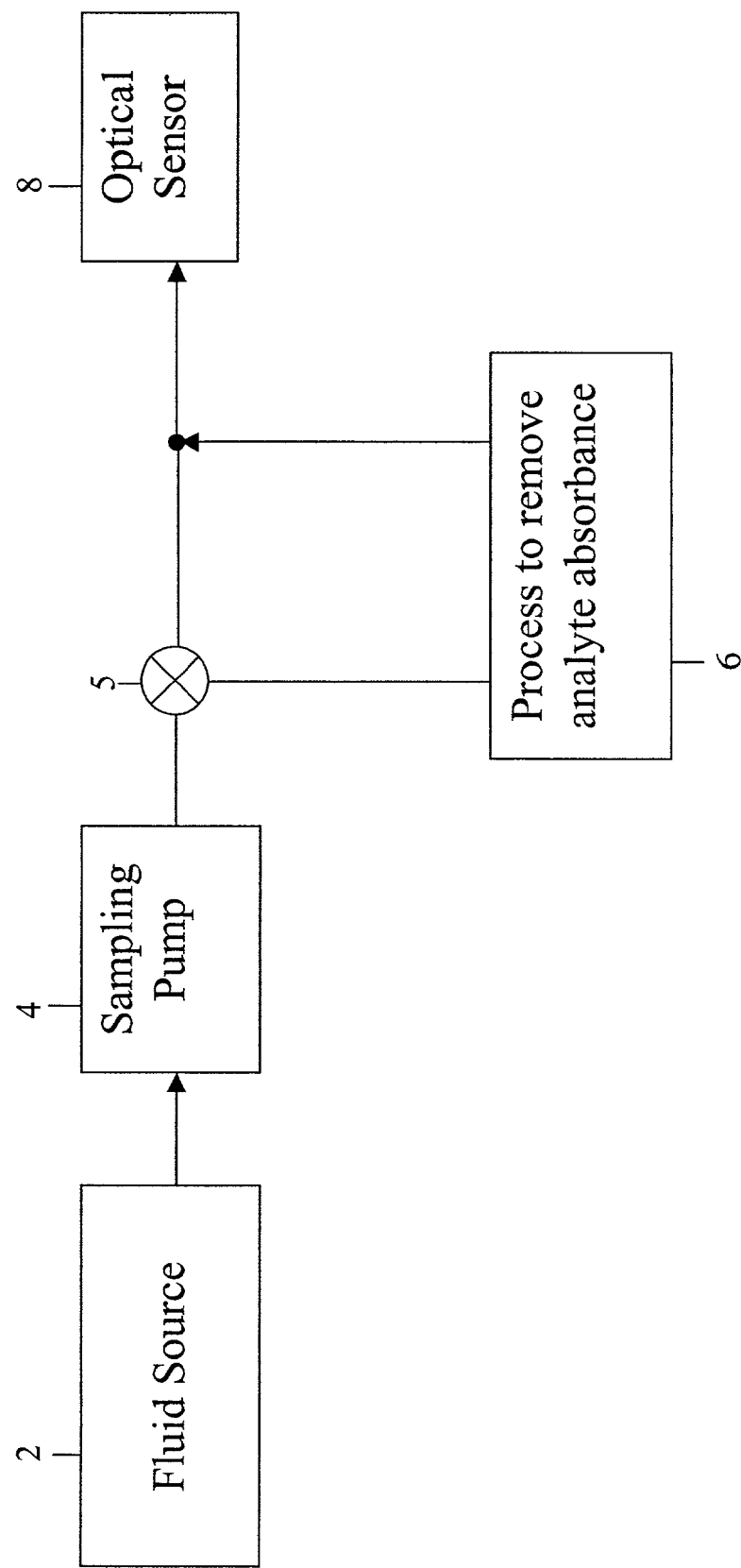
FIG. 1 illustrates a black box diagram of an embodiment of a system for measuring a constituent in a fluid using a process that selectively removes the intrinsic optical absorbance of the analyte.
Figure 2:
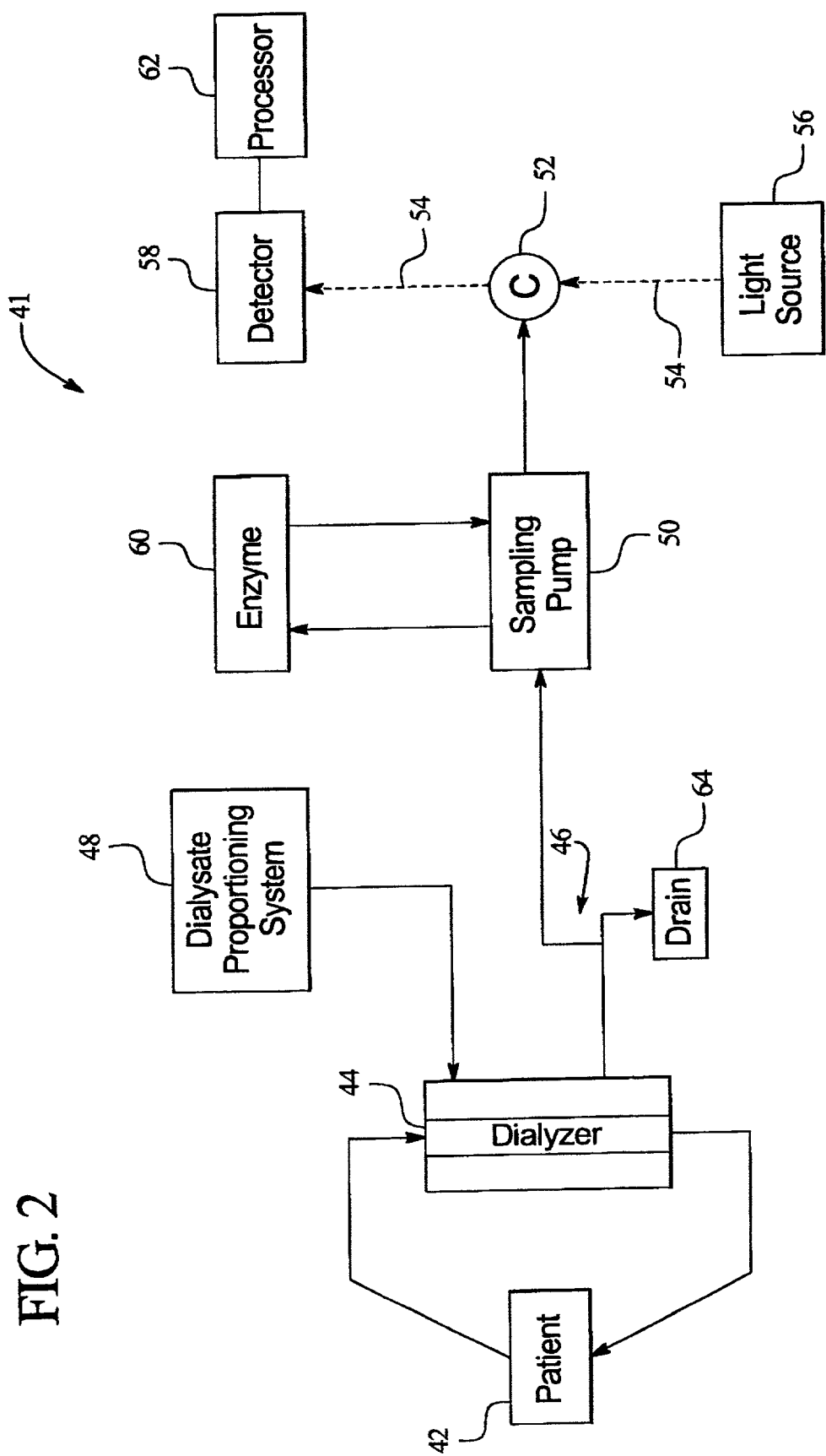
FIG. 2 illustrates a black box diagram of an embodiment of a system for measuring a constituent in effluent dialysate using optical absorbance and an enzyme.

Referring now to the drawings, wherein like numerals refer to like parts, FIG. 1 illustrates a fluid source 2 from which a sample is drawn to determine the concentration of an analyte. The fluid source 2 may represent the patient, or therapies that deliver or process fluids from the patient, for example, intravenous infusion therapies, blood exchange and separation therapies, cardiopulmonary bypass, hemodialysis, hemodiafiltration, hemofiltration, continuous ambulatory peritoneal dialysis, automated peritoneal dialysis, and continuous flow peritoneal dialysis. The fluid source may also represent biological fluids from bioreactors or tissue engineered replacement therapies. A sampling pump 4 pumps the fluid to the optical sensor 8 that measures the optical absorbance of the fluid sample. Using a valve 5 at the output of the sampling pump, the fluid sample is either directed through a process 6 that removes the intrinsic absorbance of the analyte, or straight to the optical sensor 8. One example of this process 6 may be a biocatalytic reaction that specifically targets and removes the analyte. The optical sensor 8 measures the optical absorbance of the fluid sample before and after the process from which the analyte concentration may be determined. Referring now to FIG. 2, a "single-beam" system 41 for optical absorbance measurement is shown. A patient 42 may be connected to a dialyzer 44 during, for example, a hemodialysis therapy. Effluent dialysate from the dialyzer 44 may be directed to a drain 64 and a portion of the effluent dialysate is pumped throughout the creatinine measurement system 41. A sampling pump 50 may pump the fluid sample 46 throughout the system 41.

The fluid sample 46 may be pumped through a cuvette 52 through which an optical beam is directed. The optical cuvette may be made of a material, such as, for example, quartz or other material known to have a small absorbance at the measured wavelengths. The optical beam 54 may be generated from a light source 56 and the light passing through the cuvette may further be directed into a detector 58 so that the optical absorbance of the fluid sample 46 may be measured.

The optical light source may be, for example, a lamp, a light emitting diode, or a laser diode. The detector may be photodiode, photo-transistor or a charge coupled device. Spectral resolution of the optical beam 22 may be performed at the light source or at the light detector. Spectral resolution may be accomplished using, for example, interference filters, monochromators, diffraction gratings, prisms, or tunable filters.

The pump 50 may use various valves (not shown) to either direct the fluid sample 46 through an immobilized enzyme 60, wherein creatinine hydrolysis may occur, or to altogether bypass the enzyme. Creatinine hydrolysis is the enzymatic breakdown of creatinine which produces $NH_3$ and N-methylhydantoin. After creatinine hydrolysis occurs, the pump 50 may pump the fluid sample 46 through the cuvette 52. The optical beam 54 may again be directed through the cuvette 52 and may further be directed into the detector 58 so that the optical absorbance of the fluid sample 46 may be measured.

After the detector 58 obtains optical measurements before and after the enzymatic reaction, signals representing the optical measurements may be sent to a processor 62. The processor 62, which may contain electronic components to amplify and process the signal and may also contain a microprocessor or a digital signal processor, may analyze the signals to calculate, for example, the change in optical absorbance and a creatinine concentration of the fluid sample 46. The processor 62 may obtain signals from, or send signals back to the dialysis instrument. The data processed by the processor may be displayed to an output device, printer or may produce a signal to control a function of the system 41 or another system. The temperature of the enzymatic reaction may be controlled to increase enzyme activity and the speed of the reaction (Uwajima T and Terada O, Properties of crystalline creatinine deiminase from *Cornynebacterium lilium*, Agric. Biol. Chem. 44(8), 1787–1792, 1980).

Figure 3:
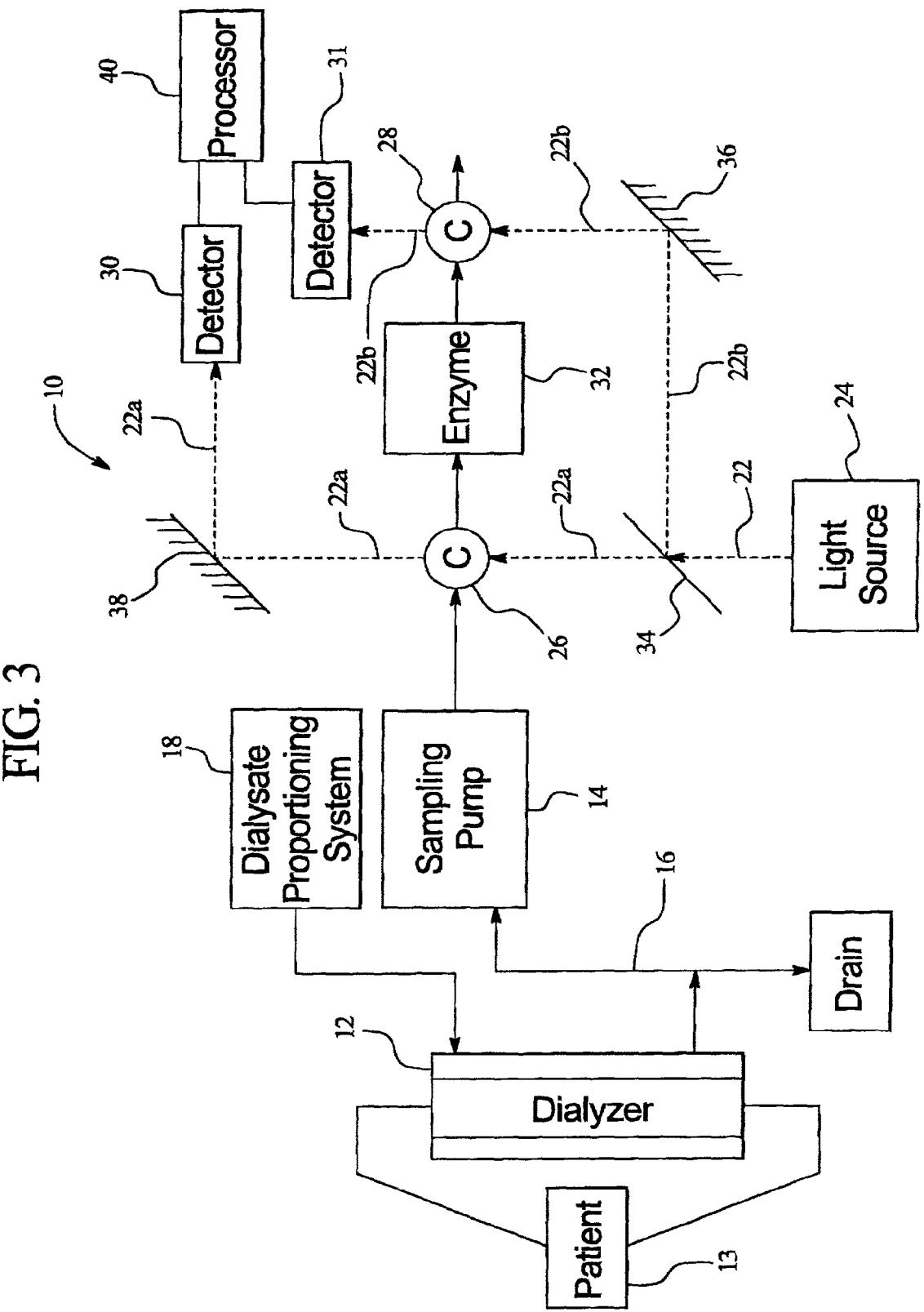
FIG. 3 illustrates a black box diagram of an embodiment of a system for measuring a constituent in effluent dialysate using optical absorbance and an enzyme.

FIG. 3 illustrates a system for creatinine measurement 10 using optical absorbance and enzymatic conversion. A fluid sample 16 of effluent dialysate may be obtained from a dialyzer 12 connected to a patient 13 during an extracorporeal treatment, for example hemodialysis. FIG. 3 further illustrates a pump 14 that may extract the fluid sample 16 from the dialyzer 12. The sampling pump 14 may be used to pump the fluid sample 16 from the dialyzer 12 through the creatinine measurement system 10. The pump 14 may or may not be an integral part of the instrumentation used to deliver the therapy to the patient. Depending on its optical absorbance, the fluid sample 16 may be diluted with fresh dialysate by extracting fresh dialysate from a proportioning system 18 within a dialysis machine. The effluent dialysate and the fresh dialysate may be combined while flowing through the pump 14 or in a mixing chamber (not shown). Alternatively, the optical pathlength of the measurement cuvettes may be reduced to avoid sample dilution with fresh dialysate.

As shown by FIG. 3, a "split-beam" mode of optical absorbance measurement may be used. The "split-beam" mode may have an optical beam 22 which may be split to permit an optical beam 22a to be directed through the fluid sample 16 before the fluid sample 16 is brought in contact with the enzyme. Another optical beam 22b of the optical beam 22 may be directed through the fluid sample 16 after the enzymatic reaction is complete. Alternatively, optical fibers may be used to split the optical beam 22.

The first cuvette 26 illustrated in FIG. 3 may be located in a path of the optical beam 22a; and the second cuvette 28 may be in a path of the optical beam 22b. The fluid sample 16 may be pumped through the first cuvette 26 as shown in FIG. 3. After the first cuvette 26, the optical beam 22a may be directed to a first mirror 38 and reflected to a detector 30 to measure optical absorbance of the fluid sample 16 prior to bringing the fluid sample 16 in contact with the enzyme.

The fluid sample 16 may also be pumped through the second cuvette 28 after passing the same through the immobilized enzyme 32 in FIG. 3. It is noted that another chemical process that specifically binds and partially or completely removes the analyte may be used, instead of the enzyme, as the chemical recognition component. Again, the optical beam 22b may be directed to a second mirror 36 and reflected to a second detector 31 to measure optical absorbance of the fluid sample 16 after enzymatic conversion. The optical beam 22b may proceed from the second cuvette 28 to the second detector 31.

FIG. 3 illustrates the optical beam 22 directed through a beam splitter 34 which splits the optical beam 22 into the optical beams 22a and 22b. After the optical beam 22 is split by the beam splitter 34, the optical beam 22a may further be directed through the first cuvette 26. After being directed through the first cuvette 26, the optical beam 22a may be reflected from the first mirror 38 and to the light detector 30. After the optical beam 22 is split by the beam splitter 34, the optical beam 22b may be reflected from the second mirror 36 through the second cuvette 28 to the second light detector 31. The light detector may contain multiple detection elements (such as photodiodes) to measure light intensity from separate light beams 22a and 22b.

FIG. 3 further illustrates the contact of the fluid sample 16 with the enzyme immobilized on a substrate. Enzyme immobilization can be accomplished using several well known methods in the art (ref. Killard et al. Trends in biotechnology, 2000). The enzyme, may be, for example, creatinine deiminase which may facilitate the hydrolysis of the creatinine in the fluid sample 16. The fluid sample 16 may be directed through the first cuvette 26 for a subsequent optical absorbance measurement by the detector 30. After being directed through the first cuvette 26, the fluid sample 16 may be directed through the immobilized enzyme where creatinine hydrolysis occurs. After converting creatinine in the fluid sample 16 to N-methlyhydantoin and $NH_3$ using creatinine deiminase, the sample may be directed through the second cuvette 28 for an optical absorbance measurement by the second detector 31. After measurement, the sample may then be sent via the dialysate stream to a drain (not shown).

A microprocessor or digital signal processor 40 may receive signals from the detectors 30 and 31 representing the optical absorbance of the fluid sample 16 before and after enzymatic conversion. The signals may be analyzed by the processor 40 to calculate, for example, the difference in absorbance of the biocatalytic process, and a creatinine concentration of the fluid sample 16. The results of the calculation may be displayed to an output device which may be an integral part of the instrument performing the therapy, or to a separate device such as a printer. Alternatively, the results of the calculation may produce a signal to control a function of the system 10 or another system.

Using the creatinine measurement systems 10 or 41, creatinine concentration may be measured in effluent dialysate continuously or intermittently. The kinetics of creatinine removal in dialysate may be used to estimate changes in patient lean body mass, and whole-body clearance which are essential for delivering adequate dialysis.

The method for creatinine measurement was tested using solutions of creatinine deiminase and creatinine prepared in the laboratory. Optical absorbance spectra of these solutions were measured using a UV/VIS spectrophotometer, model CE2014 from Cecil Instruments. The absorbance of creatinine, creatinine deiminase, and N-methylhydantoin were separately measured. Subsequently, creatinine deiminase and creatinine were mixed in equal volumes and the optical absorbance of the mixture was measured after creatinine hydrolysis was complete.

Figure 4:
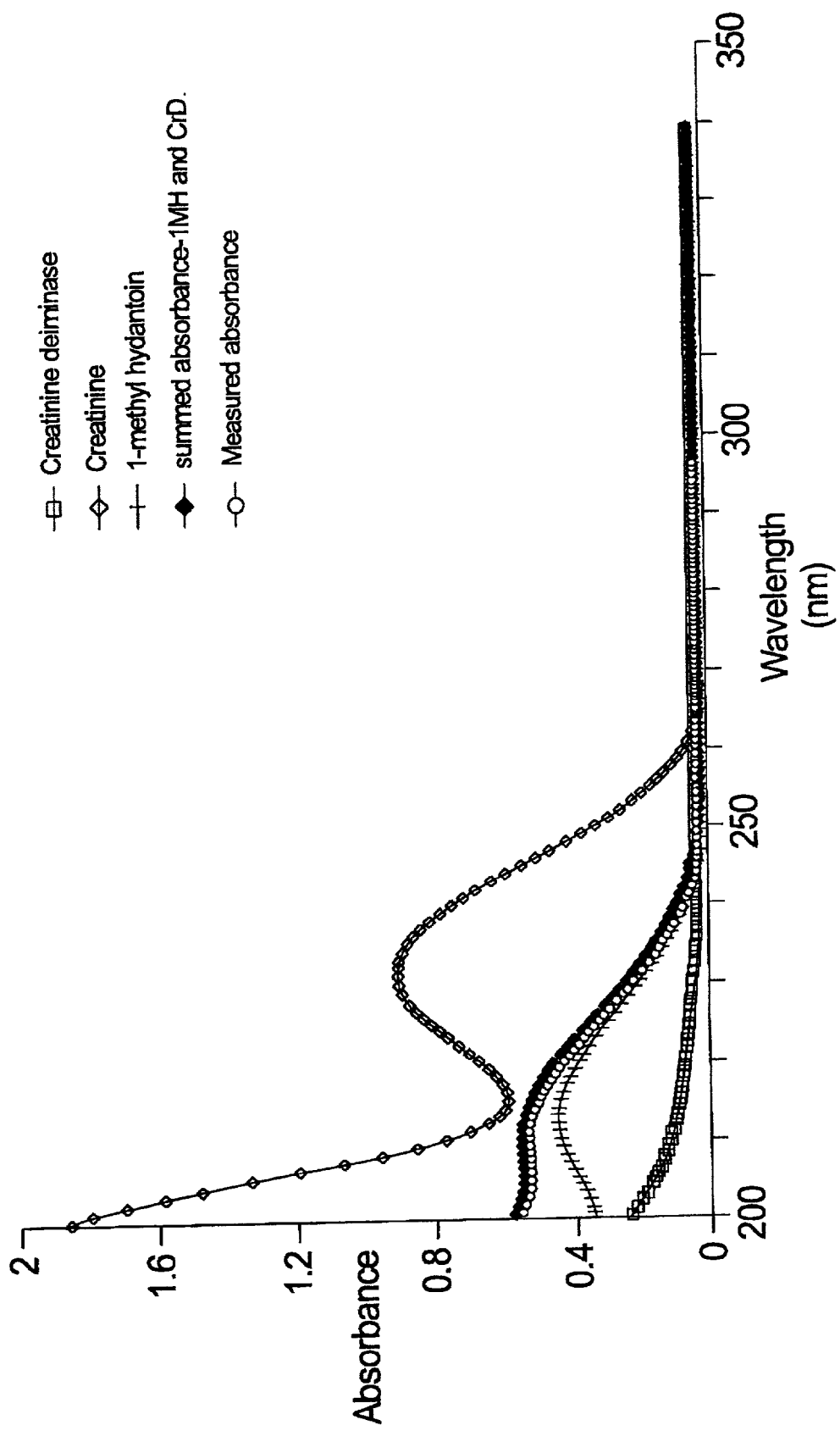
FIG. 4 illustrates a graph of an embodiment showing a measured optical absorbance spectra of creatinine, creatinine deiminase, N-methylhydantoin, and a summed optical absorbance of N-methylhydantoin and creatinine deiminase.

FIG. 4 illustrates a graph of the optical absorbance spectra of creatinine, and creatinine deiminase measured separately. A solution of N-methylhydantoin was prepared at a concentration expected from the creatinine deiminase reaction and the absorbance of the solution was measured. FIG. 4 also illustrates the absorbance spectrum of N-methylhydantoin and the summed absorbance spectrum of creatinine deiminase and N-methylhydantoin.

The results show that the absorbance spectrum of creatinine (measured before adding creatinine deiminase) is significantly different from that of N-methylhydantoin. After mixing the solutions of creatinine and creatinine deiminase, the absorbance of the solution is equal, within experimental error, to the sum of the separately measured absorbance spectra of N-methylhydantoin and creatinine deiminase. Therefore, the disappearance of creatinine and its corresponding absorbance is accounted for by the stoichiometric appearance of N-methylhydantoin. This also indicates that $NH_3$ had no detectable absorbance in the measured UV spectrum.

FIGS. 5–8 illustrate further absorbance measurements of creatinine in fresh bicarbonate dialysate in combination with certain substances found in effluent dialysate and that have known interfering absorbance spectra. Uracil, uric acid and hippuric acid were added to fresh bicarbonate dialysate to produce a "background" interfering absorbance.

Figure 5:
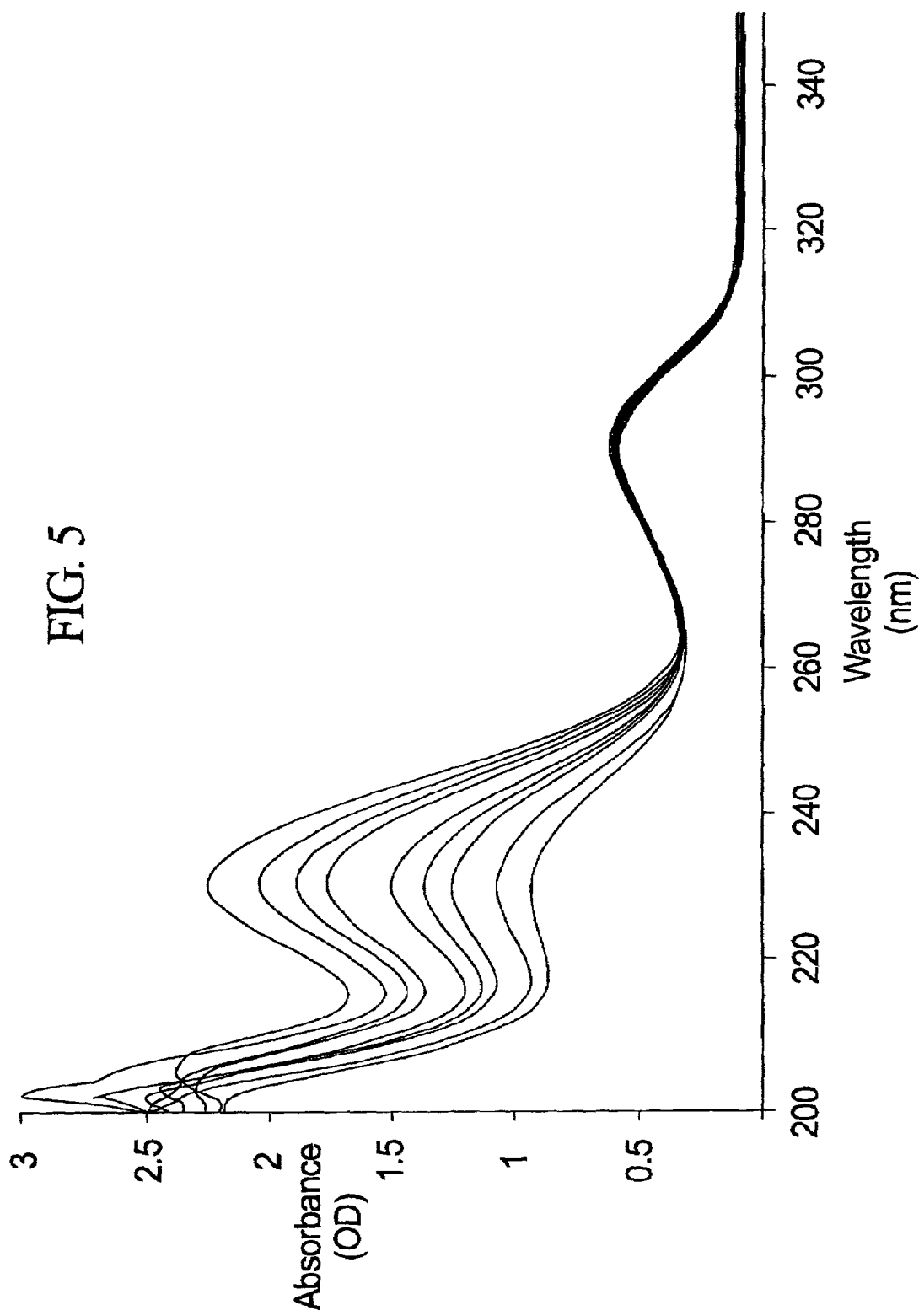
FIG. 5 illustrates a graph of an embodiment showing absorbance spectra of solutions prepared in the laboratory containing creatinine, at various concentrations, and a few interfering solutes known to exist in effluent dialysate.

Creatinine was added to this mixture of interfering solutes in concentrations ranging from 0 to 20 mmol/L. Optical absorbance spectra of these solutions are illustrated in FIG. 5. To these solutions, creatinine deiminase was added in equal volumes and compared with sample solutions which were also diluted to the same level using fresh dialysate. The resulting optical absorbance spectra of the solutions after adding creatinine deiminase are illustrated in FIG. 6.

Figure 6:
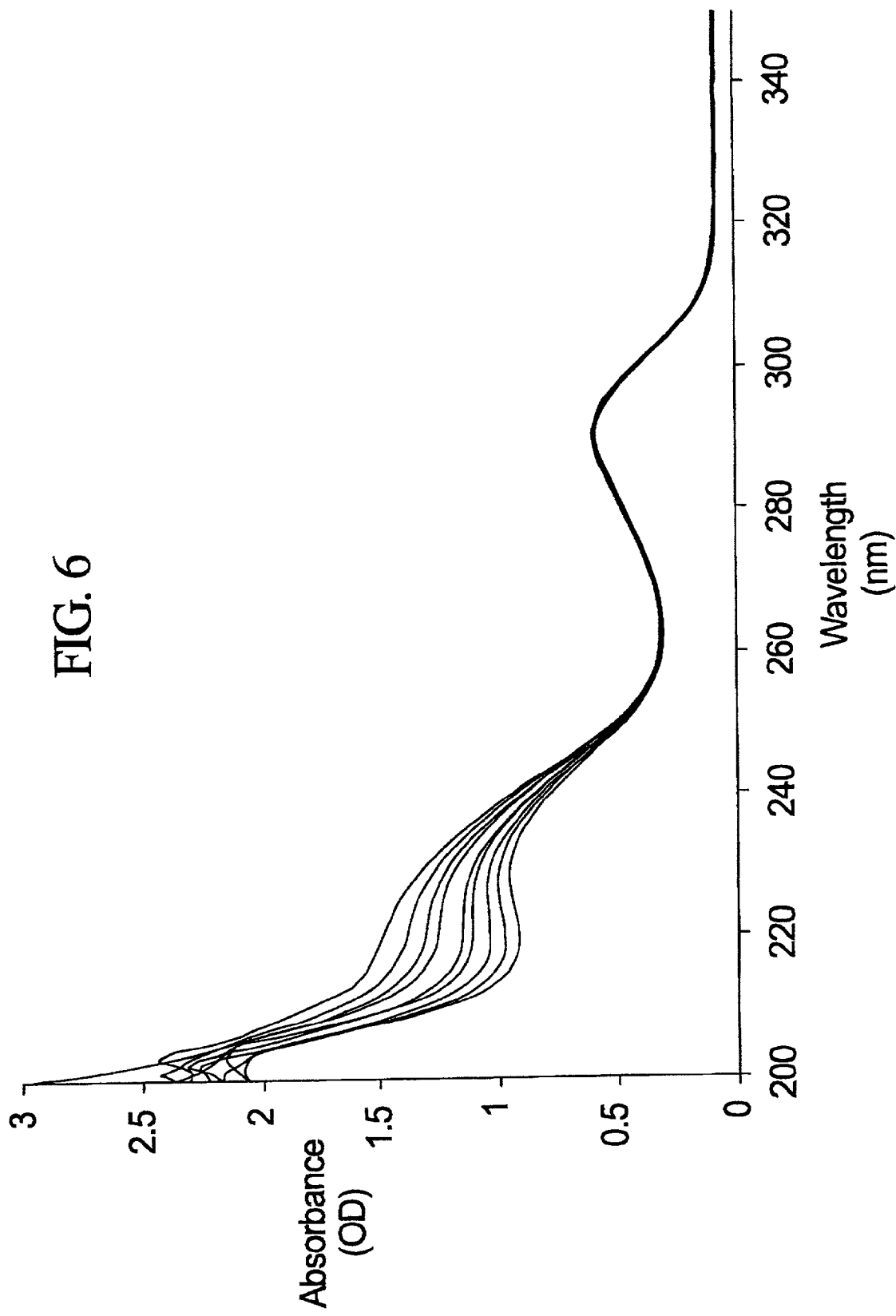
FIG. 6 illustrates a graph of an embodiment showing absorbance spectra of the solutions in FIG. 5 after adding creatinine deiminase.
Figure 7:
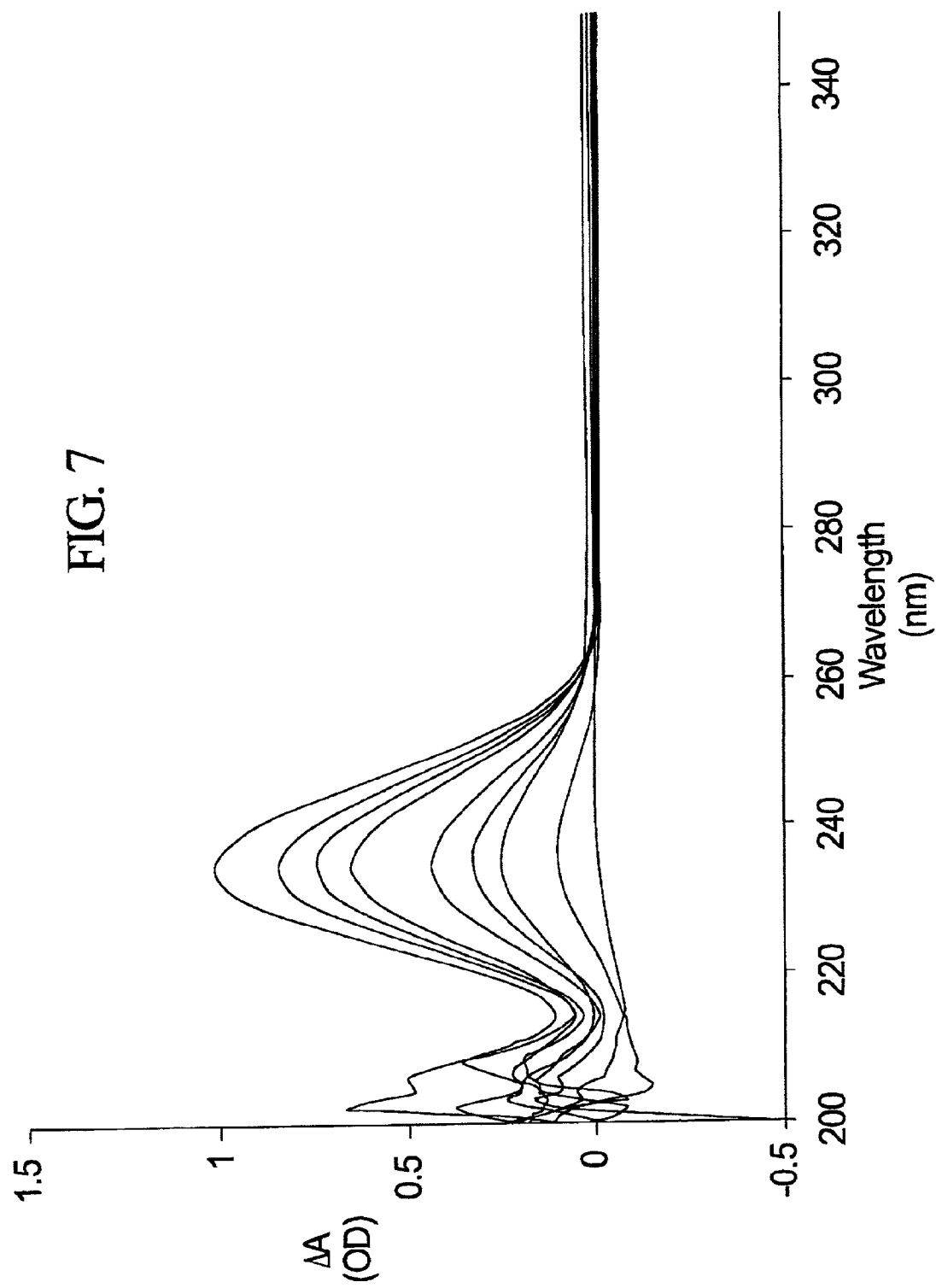
FIG. 7 illustrates a graph of an embodiment showing the difference between absorbance spectra illustrated in FIG. 5 and FIG. 6 respectively.

FIG. 7 illustrates a graph of the difference between the absorbance spectra measured before the creatinine deiminase reaction (FIG. 5) and after the creatinine deiminase reaction (FIG. 6). FIG. 7 further illustrates the fact that the absorbance maxima in the difference spectra occur at 236 nm, consistent with the largest absorbance peak in the creatinine absorbance spectrum.

Figure 8:
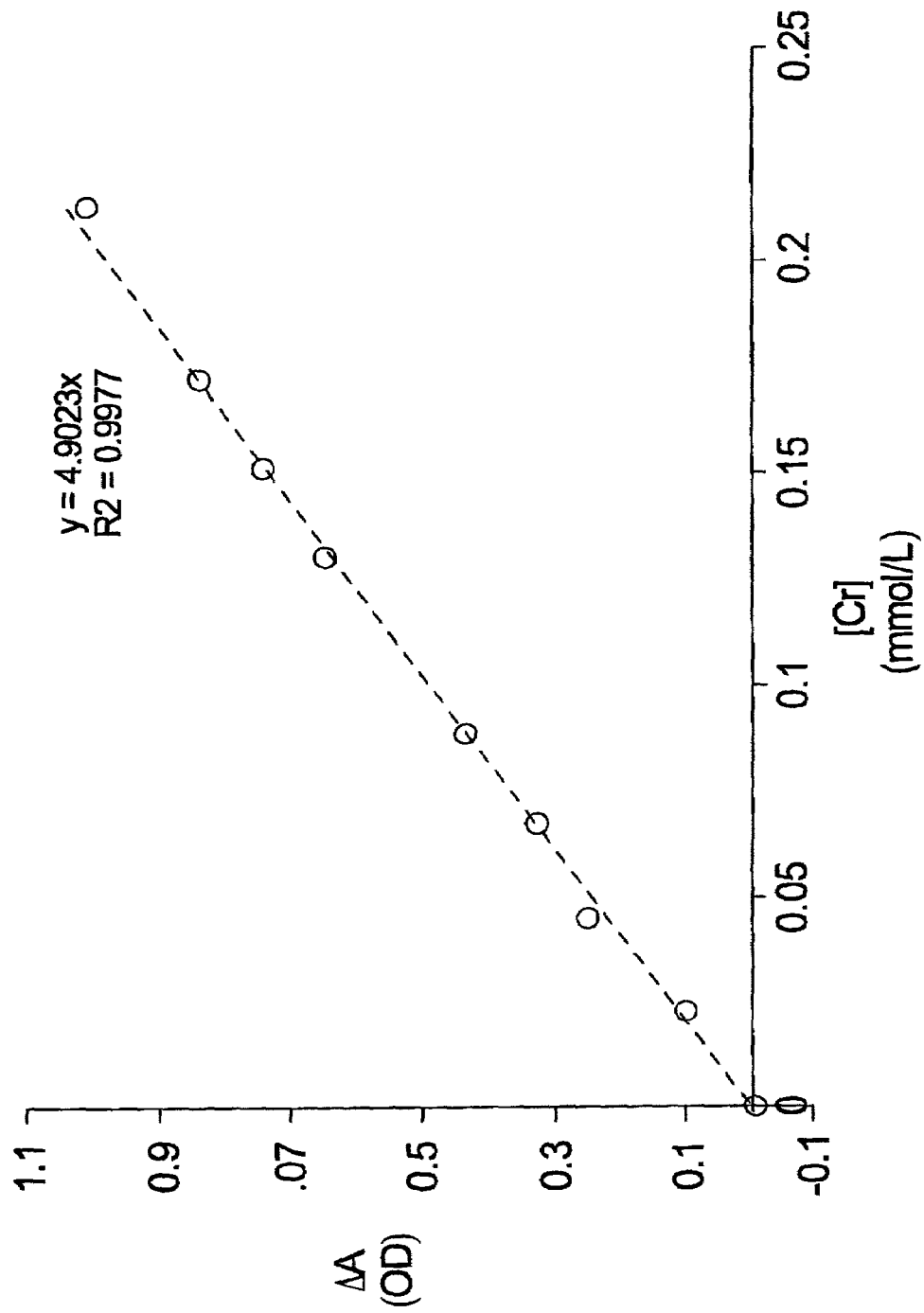
FIG. 8 illustrates a graph of an embodiment showing a correlation of absorbance maxima in FIG. 7 and creatinine concentration.

FIG. 8 illustrates a graph of the correlation of the absorbance maxima in the difference absorbance spectra and creatinine concentration. FIG. 8 further illustrates that the slope of the straight line is equal to the difference in the molar extinction coefficients of creatinine and N-methylhydantoin measured separately.

Figure 9:
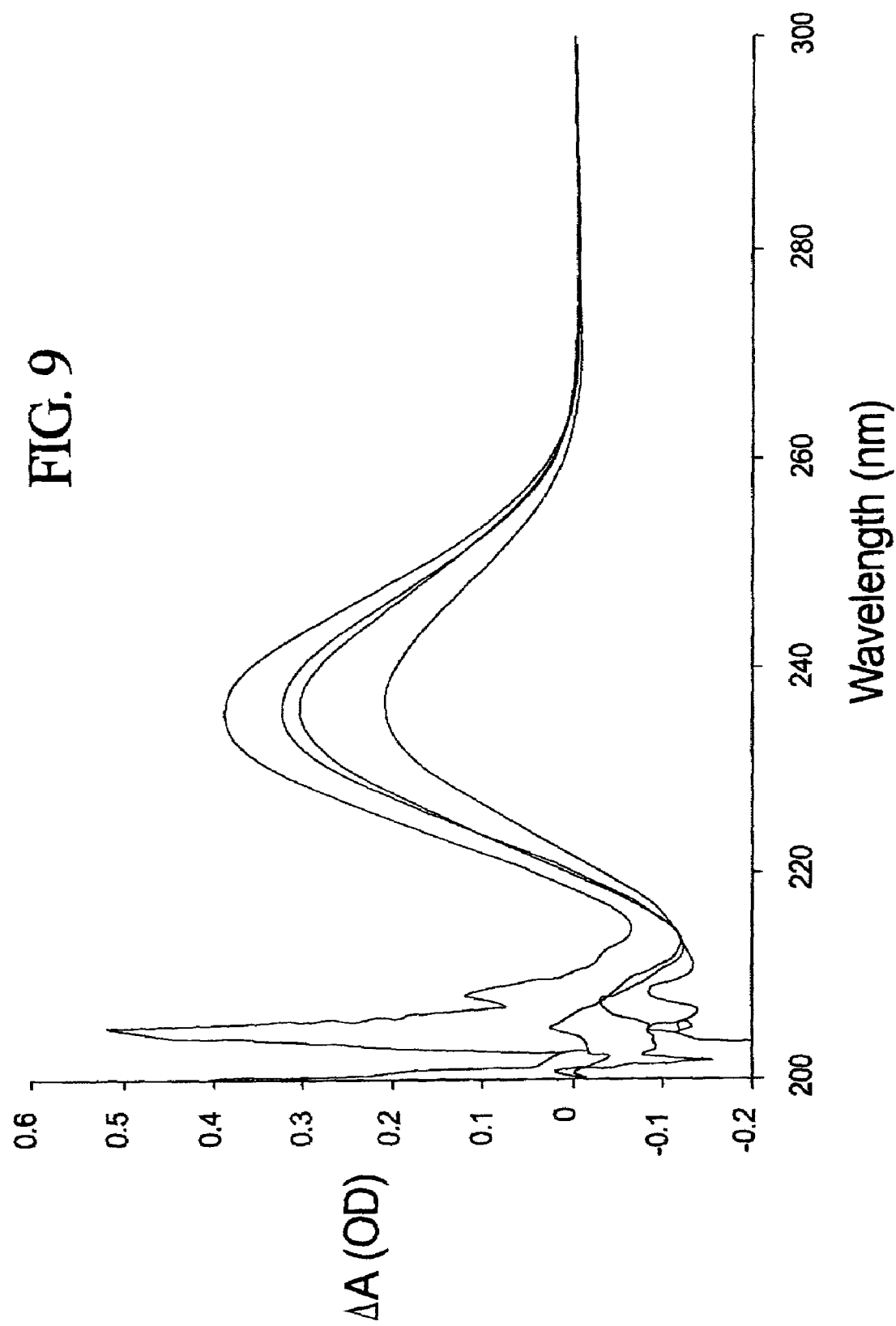
FIG. 9 illustrates a graph of an embodiment showing the change in optical absorbance measured as a result of adding creatinine deiminase to four samples of effluent dialysate collected from a hemodialysis patient.
Figure 10:
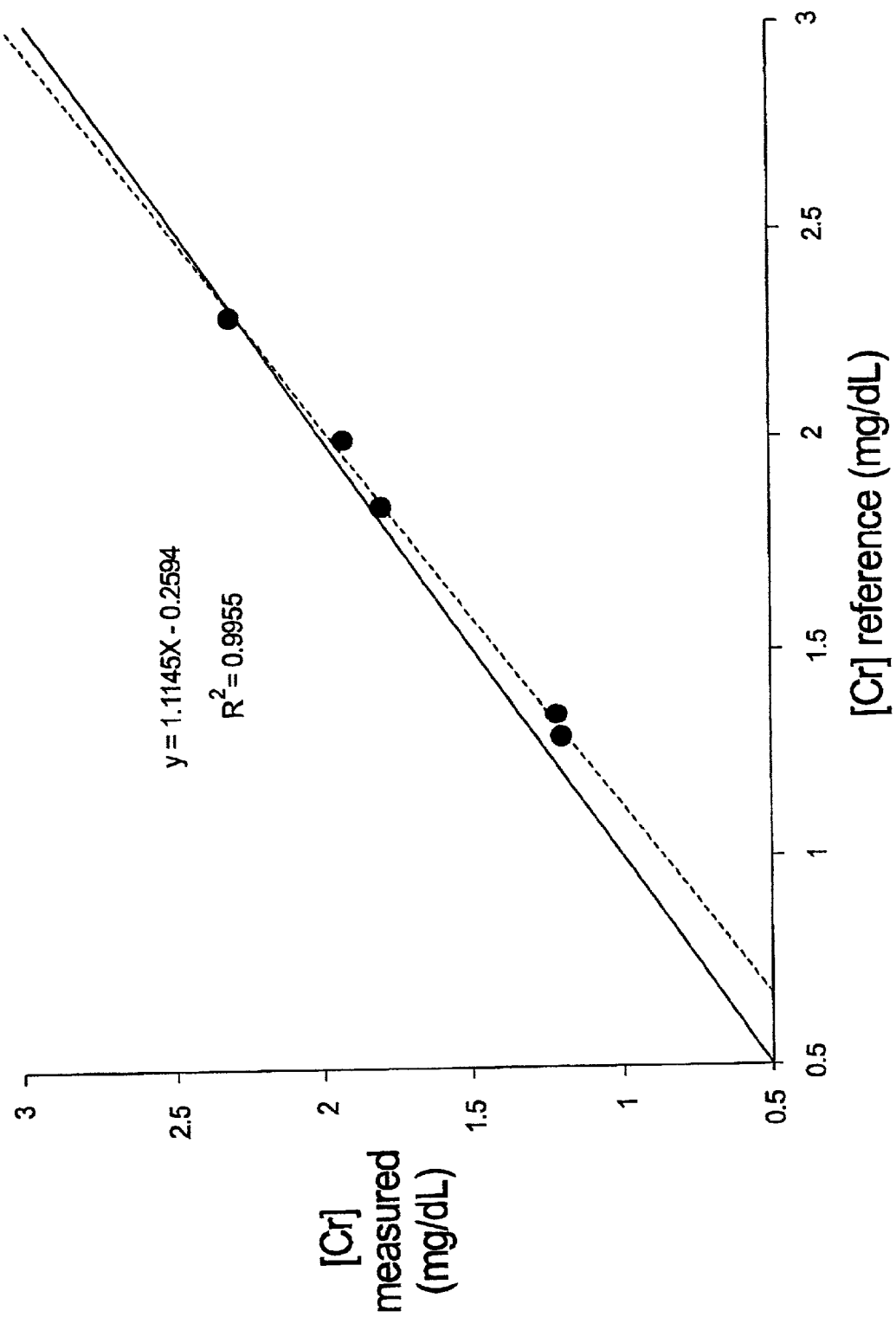
FIG. 10 illustrates a graph of an embodiment showing the measurement accuracy of creatinine from the absorbance spectra of FIG. 9.

FIG. 9 illustrates different absorbance spectra (i.e. similar to FIG. 7) measured in effluent dialysate from a hemodialysis patient. Four samples of effluent dialysate were collected through a 0.2 micron syringe filter at 30, 60, 90 and 180 minutes of dialysis and refrigerated prior to analysis. Creatinine deiminase was added to the samples and the change in absorbance was measured, in a 0.5 cm optical cuvette, using a spectrophotometer. From the difference absorbance spectra the concentration of creatinine was estimated using the calibration equation obtained from FIG. 8. The estimated creatinine concentration was compared against creatinine measured using the Jaffé reference method (alkaline sodium picrate reaction), and is illustrated in FIG. 10. The close agreement between the two methods ($r^2$=0.99) and the measured average error of 4% indicates that creatinine can be measured accurately using its intrinsic absorbance and used to measure creatinine kinetics during dialysis.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims.

We claim:

1. A system for measuring an analyte in a biological fluid using an intrinsic optical absorbance of the analyte, the system comprising:
   a fluid sample containing an analyte;
   a light source forming an optical beam that is directed on a route through the fluid sample;
   a reactor that selectively removes the optical absorbance of the analyte wherein the analyte has a first optical absorbance before the removal and further having a second optical absorbance after the removal; and
   a light detector receiving the optical beam directed through the fluid sample to produce a first signal indicative of the first optical absorbance and receiving the optical beam directed through the fluid sample after the removal to produce a second signal indicative of the second optical absorbance.

2. The system of claim 1 further comprising:
   a processor comparing the first optical absorbance to the second optical absorbance.

3. The system of claim 1 further comprising:
   a cuvette through which the fluid sample is directed.

4. The system of claim 1 further comprising:
   a cuvette through which the fluid sample is directed after the process.

5. The system of claim 1 wherein the reactor includes an enzyme.

6. The system of claim 1 further comprising:
   a beamsplitter in the route of the optical beam separating the optical beam into a first beam and a second beam.

7. The system of claim 1 further comprising:
   a mirror in the route of the optical beam, the mirror reflecting the optical beam to the light detector.

8. The system of claim 1 wherein multiple analytes from the fluid sample are measured.

9. The system of claim 1 wherein an optical cuvette is associated with a valve to measure the fluid sample before and after the removal.

10. The system of claim 5 wherein the enzyme is immobilized.

11. A method for measuring creatinine, the method comprising the steps of:
    pumping a substance through an optical beam;
    detecting a first optical absorbance of the substance;
    combining the substance with creatinine deiminase;
    detecting a second optical absorbance of the substance combined with creatinine deiminase; and
    comparing the first optical absorbance to the second optical absorbance.

12. The method of claim 11 further comprising the step of:
    pumping the substance through a cuvette.

13. The method of claim 11 further comprising the step of:
    directing the optical beam with an optical waveguide.

14. The method of claim 11 further comprising the step of:
    reflecting the optical beam with a mirror.

15. The method of claim 11 further comprising the step of:
    directing the optical beam with a beam splitter that splits the optical beam into a first beam and a second beam.

16. The method of claim 11 further comprising the step of:
    obtaining the substance from a body fluid, body secretion or from clinical therapies for example renal-replacement.

17. The method of claim 11 further comprising the step of:
    obtaining the substance from a patient.

18. The method of claim 11 further comprising the step of:
    intermittently measuring the first optical absorbance and the second optical absorbance.

19. The method of claim 11 further comprising the step of:
    continuously measuring the first optical absorbance and the second optical absorbance.

20. The method of claim 11 wherein creatinine deiminase is combined with creatinine in the substance to produce at least one of N-methylhydantoin and $NH_3$.

21. The system of claim 5 wherein the enzyme is creatinine deiminase.

* * * * *